United States Patent
Satoh et al.

(10) Patent No.: US 11,600,378 B2
(45) Date of Patent: Mar. 7, 2023

(54) IMAGE DIAGNOSIS SUPPORT APPARATUS, IMAGE DIAGNOSIS SUPPORT PROGRAM, AND MEDICAL IMAGE ACQUISITION APPARATUS INCLUDING THE SAME

(71) Applicant: Hitachi, Ltd., Tokyo (JP)

(72) Inventors: Ryota Satoh, Tokyo (JP); Tomoki Amemiya, Tokyo (JP); Toru Shirai, Tokyo (JP); Yoshitaka Bito, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 221 days.

(21) Appl. No.: 16/896,309

(22) Filed: Jun. 9, 2020

(65) Prior Publication Data
US 2021/0193299 A1    Jun. 24, 2021

(30) Foreign Application Priority Data
Dec. 23, 2019 (JP) .............................. JP2019-231677

(51) Int. Cl.
*G16H 30/40* (2018.01)
*G06T 7/00* (2017.01)
(Continued)

(52) U.S. Cl.
CPC ........... *G16H 30/40* (2018.01); *A61B 5/0042* (2013.01); *A61B 5/055* (2013.01); *G06N 20/00* (2019.01); *G06T 7/0014* (2013.01); *G06T 2207/30016* (2013.01); *G06T 2207/30096* (2013.01)

(58) Field of Classification Search
CPC ........ G16H 30/40; G16H 50/20; G06N 20/00; A61B 5/0042; A61B 5/005; G06T 7/0014;
(Continued)

(56) References Cited

U.S. PATENT DOCUMENTS

2003/0161497 A1* 8/2003 Vuylsteke ................. G06T 5/30
382/100
2009/0083072 A1* 3/2009 Osawa ..................... G16H 70/60
705/2
(Continued)

FOREIGN PATENT DOCUMENTS

JP    2007275440 A    10/2007

OTHER PUBLICATIONS

Kononenko. "Machine learning for medical diagnosis: history, state of the art and perspective", Artificial Intelligence in Medicine, vol. 23, Issue 1, Aug. 2001 (Year: 2001).*
(Continued)

*Primary Examiner* — Vu Le
*Assistant Examiner* — Julius Chai
(74) *Attorney, Agent, or Firm* — Mattingly & Malur, PC

(57) ABSTRACT

The most appropriate image for a diagnostic target among a plurality of images is selected and accurate diagnosis support information is presented regardless of the type of a selected image, a modality, or the like. An image diagnosis support apparatus includes: a diagnostic information generation unit that generates diagnostic information based on a plurality of medical images; a reliability calculation unit that evaluates an image quality and calculates an image reliability for each of the plurality of medical images; and a degree-of-contribution calculation unit that calculates a degree of contribution of each of the plurality of medical images to the diagnostic information using an internal parameter indicating a degree of appropriateness of each medical image for a diagnostic target and the reliability calculated by the reliability calculation unit. An image for detection used by the diagnostic information generation unit is generated based on the degree of contribution.

10 Claims, 14 Drawing Sheets

(51) Int. Cl.
*A61B 5/055* (2006.01)
*G06N 20/00* (2019.01)
*A61B 5/00* (2006.01)

(58) Field of Classification Search
CPC ......... G06T 7/0012; G06T 2207/30016; G06T 2207/30096
See application file for complete search history.

(56) References Cited

U.S. PATENT DOCUMENTS

| | | | |
|---|---|---|---|
| 2011/0122146 A1* | 5/2011 | Nie | G06T 5/004 |
| | | | 345/589 |
| 2012/0054652 A1* | 3/2012 | Kawagishi | G16H 50/20 |
| | | | 715/764 |
| 2016/0364857 A1* | 12/2016 | Reicher | A61B 10/02 |
| 2016/0364862 A1* | 12/2016 | Reicher | G06K 9/6227 |
| 2018/0101644 A1* | 4/2018 | Hammes | A61B 5/055 |
| 2018/0137244 A1* | 5/2018 | Sorenson | G16H 30/40 |
| 2020/0342990 A1* | 10/2020 | Ichinose | G06N 20/00 |
| 2021/0022689 A1* | 1/2021 | Makino | A61B 6/4007 |

OTHER PUBLICATIONS

Yicheng Chen, et al., "Toward Automatic Detection of Radiation-Induced Cerebral Microbleeds Using a 3D Deep Residual Network", Journal of Digital Imaging, Published online: Dec. 3, 2018, https://doi.org/10.1007/s10278-018-0146-z.

* cited by examiner

FIG. 7

|  | IMAGE 1 | IMAGE 2 | IMAGE 3 | IMAGE 4 | IMAGE 5 |
|---|---|---|---|---|---|
| LESION A | 1.0 | 0.2 | 0.9 | 0.9 | 0.7 |
| LESION B | 0.2 | 1.0 | 0.7 | 0.7 | 0.9 |
| LESION C | 0.2 | 0.7 | 0.7 | 0.2 | 1.0 |
| LESION D | 0.7 | 0.9 | 0.2 | 1.0 | 0.2 |

IMAGE DIAGNOSIS SUPPORT APPARATUS, IMAGE DIAGNOSIS SUPPORT PROGRAM, AND MEDICAL IMAGE ACQUISITION APPARATUS INCLUDING THE SAME

INCORPORATION BY REFERENCE

The present application claims priority from Japanese patent application JP-2019-231677 filed on Dec. 23, 2019, the content of which is hereby incorporated by reference into this application.

BACKGROUND OF THE INVENTION

Field of the Invention

The present invention relates to a technique for performing diagnosis support using an image acquired by a medical image acquisition apparatus, such as a magnetic resonance imaging apparatus (hereinafter, referred to as an MRI apparatus), an X-ray imaging apparatus, and a CT apparatus.

Description of the Related Art

In the medical field, image diagnosis for diagnosing a disease or a lesion based on an image captured by an MRI apparatus or a CT apparatus is widely performed. In recent years, a diagnosis support technique for determining the presence or absence of a lesion, the degree of progress of a lesion, the degree of malignancy of a lesion, or the like in a measured image using an AI learned by machine learning has been developed (Chen Y et al., "Toward Automatic Detection of Radiation-Induced Cerebral Microbleeds Using a 3D Deep Residual Netword", J Digit Imaging, October, 2019, 32 (5) 766-772, or the like).

In image diagnosis support using machine learning, the presence or absence of a lesion or the like is determined using an AI, which has learned the relationship between the type or part of disease and an image for each type or part of disease, with one or a plurality of measured images as input. Chen Y et al., "Toward Automatic Detection of Radiation-Induced Cerebral Microbleeds Using a 3D Deep Residual Netword", J Digit Imaging, October, 2019, 32 (5) 766-772 discloses a technique for automatically detecting a small blood vessel lesion in the brain by a machine learning model learned using a magnetic susceptibility weighted image (SWI) acquired by an MRI apparatus.

In image diagnosis, there is an imaging method or an image type suitable for diagnosis depending on a disease or a lesion. For this reason, it is necessary to select an image or an image type of an appropriate modality according to a diagnostic target. For example, as MRI images, various images having different tissue contrasts, such as a T1 weighted image (T1W), a T2 weighted image (T2W), and a magnetic susceptibility weighted image (SWI), can be acquired by converting imaging conditions. Which image type is better for detection of which lesion depends.

On the other hand, in order to improve the accuracy of diagnosis of a disease or a lesion, it is known that it is effective to refer to not only one image but also a plurality of types of images or images acquired by a plurality of modalities. JP-A-2007-275440 discloses a technique for presenting an index indicating which of a plurality of modalities is effective in order to objectively indicate which modality image is effective for a diagnostic target.

At the time of image diagnosis, when a plurality of types of images are measured for the same subject and one or a plurality of images most suitable for the diagnostic target are selected from the plurality of types of images and used, artifacts may be caused in a part or a region to be diagnosed in the image to be selected due to the influence of body motion, imaging conditions, and the like. As a result, there will be cases where the selected images cannot be used for diagnosis. In this case, it is conceivable to use other images, but the selection is not easy. This problem is the same even for images acquired by modalities of different image types, for example, MR images, CT images, X-ray images, and the like, and cannot be solved even by the technique described in JP-A-2007-275440.

In addition, even when a predetermined image is selected, the image contrast differs depending on the manufacturer (vendor) of the medical image acquisition apparatus or imaging conditions. For example, in the case of an MRI apparatus, the image contrast varies due to differences in magnetic field strength or imaging parameters. Since the selected image is not always the same as the contrast of an image used when creating the learned AI, it is not possible to perform accurate image diagnosis support in a case in which the known AI is used.

SUMMARY OF THE INVENTION

It is an object of the invention to provide means for selecting the most appropriate image for a diagnostic target among a plurality of images and to provide means capable of presenting accurate diagnosis support information regardless of the type of a selected image, a modality, or the like.

In order to solve the aforementioned problem, according to a first aspect of the invention, there is provided means for automatically selecting an image using two indices, that is, an index (internal parameter) indicating appropriateness for a diagnostic target and an index (reliability) relevant to the image quality of the image itself.

According to a second aspect of the invention, there is provided means for converting an image, which is selected for diagnosis support for a predetermined diagnostic target, into an input image of a learned AI learned for the diagnostic target.

That is, the image diagnosis support apparatus according to the first aspect of the invention includes: a diagnostic information generation unit that generates diagnostic information based on a plurality of medical images; a reliability calculation unit that evaluates an image quality and calculates an image reliability for each of the plurality of medical images; and a degree-of-contribution calculation unit that calculates a degree of contribution of each of the plurality of medical images to the diagnostic information using an internal parameter indicating a degree of appropriateness of each medical image for a diagnostic target and the reliability calculated by the reliability calculation unit. The image diagnosis support apparatus can further include an image-for-detection generation unit that generates an image for detection using a medical image selected by an image selection unit.

In addition, the image diagnosis support apparatus according to the second aspect further includes a contrast adjustment unit that adjusts a contrast of the medical image or the image for detection to a contrast of a specific image.

In addition, an image diagnosis support program of the invention causes a computer to execute: a step of evaluating an image quality and calculating an image reliability for each of a plurality of medical images; a step of calculating a degree of contribution of each of the plurality of medical images to a diagnostic target using an internal parameter indicating a degree of appropriateness of each medical image for the diagnostic target and the reliability; and a step of generating an image for detection, which is used for generating diagnostic information, using the plurality of medical images and the degree of contribution.

In addition, a medical image acquisition apparatus of the invention includes: an imaging unit that acquires a medical image; and an image processing unit that performs processing on the medical image acquired by the imaging unit, in which the image processing unit includes: a diagnostic information generation unit that generates diagnostic information based on a plurality of medical images; a reliability calculation unit that evaluates an image quality and calculates an image reliability for each of the plurality of medical images; and a degree-of-contribution calculation unit that calculates a degree of contribution of each of the plurality of medical images to the diagnostic information using an internal parameter indicating a degree of appropriateness of each medical image for a diagnostic target and the reliability calculated by the reliability calculation unit.

BRIEF DESCRIPTION OF THE DRAWINGS

FIG. 4A is a functional block diagram illustrating the configuration of a degree-of-contribution calculation unit and FIG. 4B is a functional block diagram illustrating the configuration of an image-for-detection generation unit;

FIG. 7 is a diagram showing an example of internal parameters stored in a storage device;

DETAILED DESCRIPTION OF THE INVENTION

Hereinafter, an embodiment of an image diagnosis support apparatus of the invention will be described with reference to the accompanying diagrams.

Figure 1:
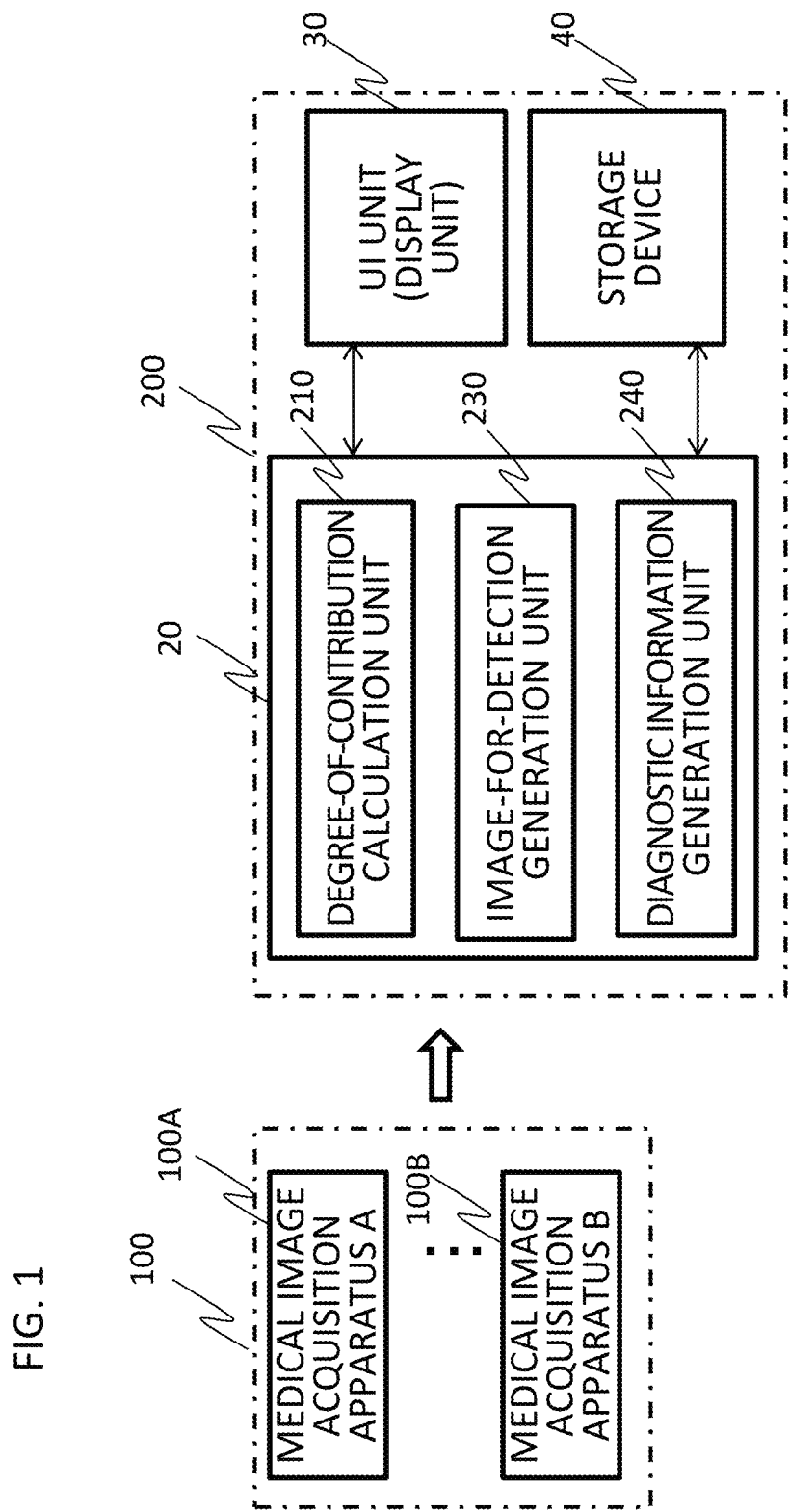
FIG. 1 is a diagram illustrating an outline of an embodiment of an image diagnosis support apparatus according to the invention.

FIG. 1 is a diagram illustrating an embodiment of the overall configuration of an image diagnosis support apparatus. An image diagnosis support apparatus 200 includes an image processing unit 20, a user interface (UI) unit 30, and a storage device 40, and receives a medical image (hereinafter, simply referred to as an image) acquired by a medical image acquisition apparatus 100, and the image processing unit 20 evaluates the input image and presents the result to the UI unit 30. The medical image acquisition apparatus 100 from which an image is received by the image diagnosis support apparatus 200 may be a single apparatus, or may be a plurality of medical image acquisition apparatuses 100A, 100B, as shown in drawings. These may be different modalities, such as an MRI apparatus, a CT apparatus, an X-ray imaging apparatus, and an ultrasonic apparatus. The image diagnosis support apparatus 200 and the medical image acquisition apparatus 100 are connected to each other by wire, wirelessly, or through a network. Alternatively, the image acquired by the medical image acquisition apparatus 100 may be input to the image diagnosis support apparatus 200 through a portable medium.

The image diagnosis support apparatus 200 can be constructed on a computer (workstation) including a CPU or a GPU, and the function of the image processing unit 20 is executed by reading a predetermined program by the computer. The UI unit 30 includes a display (display device) and input devices, such as a touch panel, a pointing device, and a keyboard, and displays a GUI or a processing result in the image processing unit 20 or receives an instruction from the user. The storage device 40 stores a processing result, or stores other pieces of data required for the processing of the image processing unit 20, and may include an external storage device, a cloud, and the like, in addition to an internal storage device of the computer.

The image processing unit 20 can have various functions relevant to image processing. In the present embodiment, the image processing unit 20 has a function of selecting the most appropriate image, among a plurality of input images, for a specific diagnostic target set through the UI unit 30 and presenting the selected image or diagnostic information derived therefrom. Here, the plurality of images may be images of a plurality of different modalities, or different types of images acquired by the same medical image acquisition apparatus, or images acquired at different times. In addition, the plurality of images may be images of different cross sections in a piece of image data or different partial images of one image.

Figure 2:
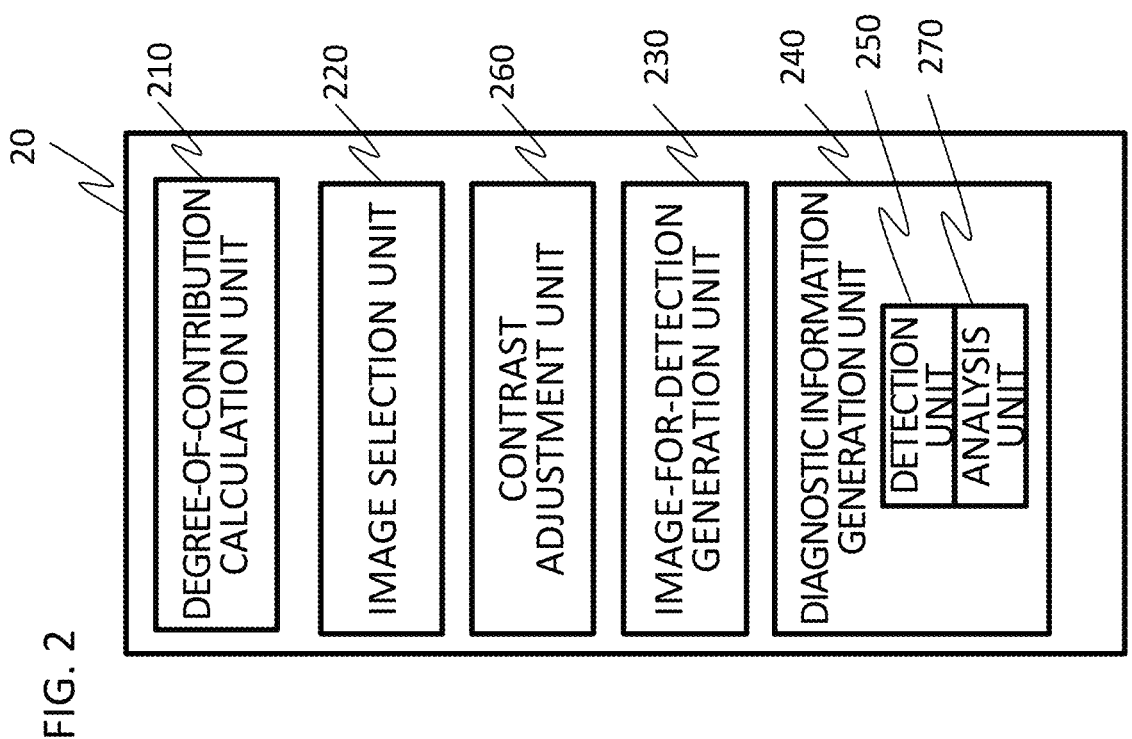
FIG. 2 is a functional block diagram illustrating details of an image processing unit.

In order to realize this function, the image processing unit 20 includes: a degree-of-contribution calculation unit 210 that calculates, for each of a plurality of images, a weighting (degree of contribution with respect to diagnostic information) considering the degree of appropriateness for a specific diagnostic target or the reliability of the image; an image-for-detection generation unit 230 that generates an image for detection from a predetermined image based on the degree of contribution; and a diagnostic information generation unit 240 that generates diagnostic information. In addition, as illustrated in FIG. 2, in order to generate an image for detection, the image processing unit 20 may include an image selection unit 220 that selects a predetermined image from a plurality of images or a contrast adjustment unit 260 that adjusts a contrast between images. In addition, the diagnostic information generation unit 240 includes, for example, a detection unit 250 that detects a lesion or an abnormality from an input image using a machine learning algorithm or an analysis unit 270 that analyzes an image.

The image for detection is an image to be input to the machine learning algorithm of the detection unit 250.

The functions of the respective units of the image processing unit 20 are realized by executing a programmed procedure by a computer, but some of the functions can be realized by hardware, such as an ASIC or an FPGA.

An operation flow of the image diagnosis support apparatus 200 having the above configuration will be described with reference to FIG. 3. First, it is assumed that a diagnostic target for the examination of a tumor in the abdomen, a vascular disorder in the brain, or the like is set by the UI unit 30. The image processing unit 20 receives a plurality of images (image group), which are examination targets and are acquired according to the examination purpose, from the medical image acquisition apparatus 100 or the storage device (S1).

The degree-of-contribution calculation unit 210 calculates the degree of contribution to the diagnostic information for each input image (S2). The degree of contribution is calculated according to a predetermined equation based on parameters (referred to as internal parameters) indicating the reliability, such as the image quality, and the degree of appropriateness of the image with respect to the diagnostic target.

Then, based on the degree of contribution, the image-for-detection generation unit 230 generates an image for detection as an input image of the detection unit 250 using the plurality of images or a predetermined image selected from the plurality of images (S3). In order to generate an image for detection, for example, an image selected by the image selection unit 220 based on the degree of contribution or an image weighted and added with the degree of contribution as a weighting is used. In addition, the image used to generate an image for detection is different in contrast from the input image (learning image) used in the learning process of the machine learning algorithm configuring the detection unit 250 due to differences in an apparatus that has acquired the image, imaging conditions, and the like. For this reason, even when the image used to generate an image for detection is input to the detection unit 250 as it is, a satisfactory result cannot be obtained. Therefore, processing for adjustment to the contrast of the learning image of the detection unit 250 is performed (contrast adjustment unit 260).

The detection unit 250 receives the image for detection generated by the image-for-detection generation unit 230, and detects the presence or absence and the degree of a lesion or abnormality (S4). The detection result is displayed on the display of the UI unit 30 (S5).

The outline of the processing of the image diagnosis support apparatus 200 has been described above, but various methods can be used for each processing. In the following embodiment, details of the processing of the image processing unit 20 will be described. In the following embodiment, a case in which a plurality of images input to the image diagnosis support apparatus 200 are images having different contrasts acquired by an MRI apparatus will be described as an example.

First Embodiment

In the present embodiment, one image is selected from a plurality of images, the image is converted into an image for detection, and then a corresponding disease or lesion is detected and presented.

Figure 4:
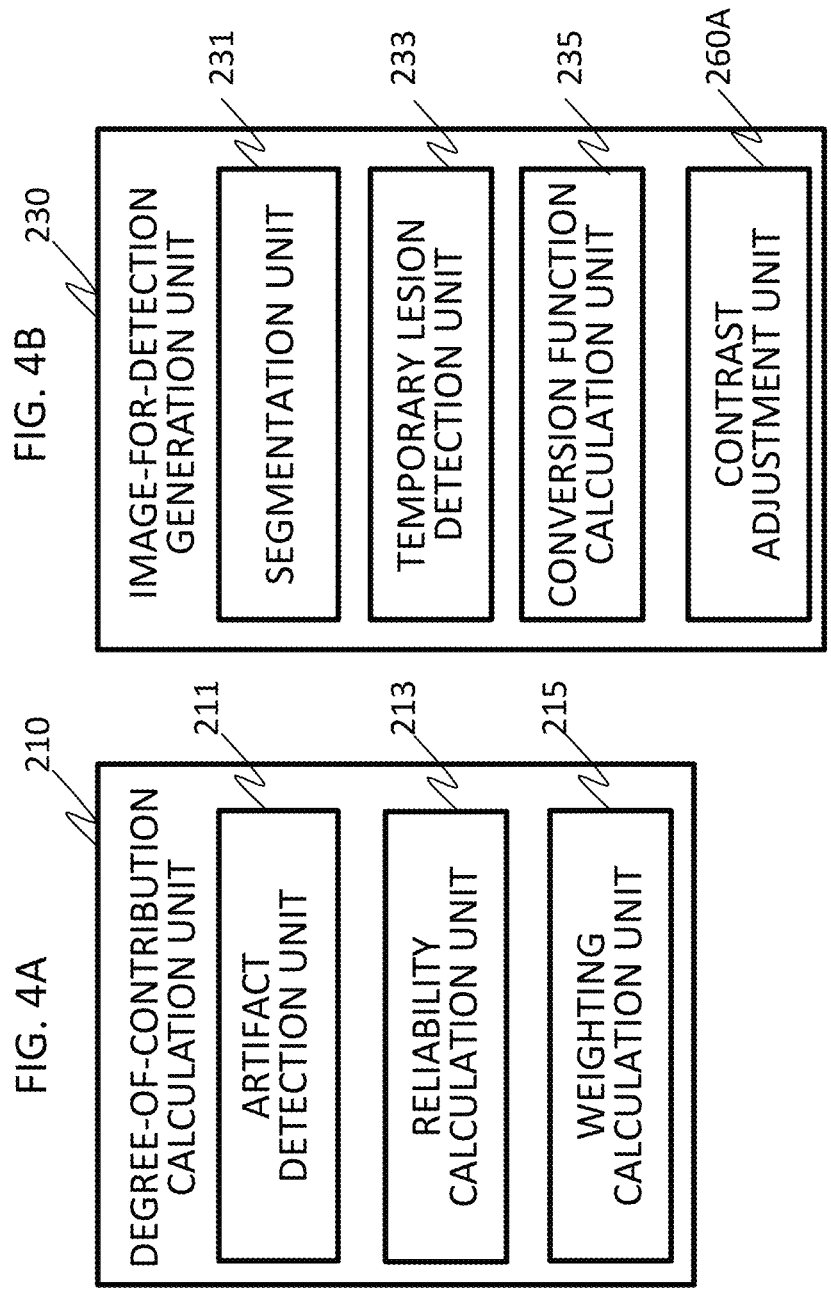
FIGS. 4A and 4B are diagrams illustrating the configuration of an image processing unit of an image diagnosis support apparatus according to a first embodiment, where

The configuration of the image processing unit 20 according to the present embodiment is the same as the configuration illustrated in FIG. 2, and includes an image selection unit 220 that selects one of a plurality of images based on the degree of contribution calculated by the degree-of-contribution calculation unit 210. In addition, the image-for-detection generation unit 230 includes a contrast adjustment unit 260A. FIGS. 4A and 4B illustrate details of the degree-of-contribution calculation unit 210 and the image-for-detection generation unit 230. The degree-of-contribution calculation unit 210 includes an artifact detection unit 211 that detects an artifact of an image, a reliability calculation unit 213 that converts the artifact into a numerical value and calculates the numerical value as a reliability, a weighting calculation unit 215 that calculates a weighting using the reliability and an internal parameter set in advance for each image. The weighting calculated by the weighting calculation unit 215 substantially indicates the degree of contribution of the image to the diagnostic information.

The image-for-detection generation unit 230 includes: a segmentation unit 231 that generates segmentation images by dividing an image selected by the image selection unit 220 for each tissue; a temporary lesion detection unit 233 that detects a portion estimated to be a lesion from the image selected by the image selection unit 220 (referred to as a selection image); a conversion function calculation unit 235 that calculates a conversion function for contrast adjustment using the segmentation images and the pixel value of the lesion part estimated by the temporary lesion detection unit 233; and a contrast adjustment unit 260A that generates an examination image by applying the conversion function to the selection image.

Figure 5:
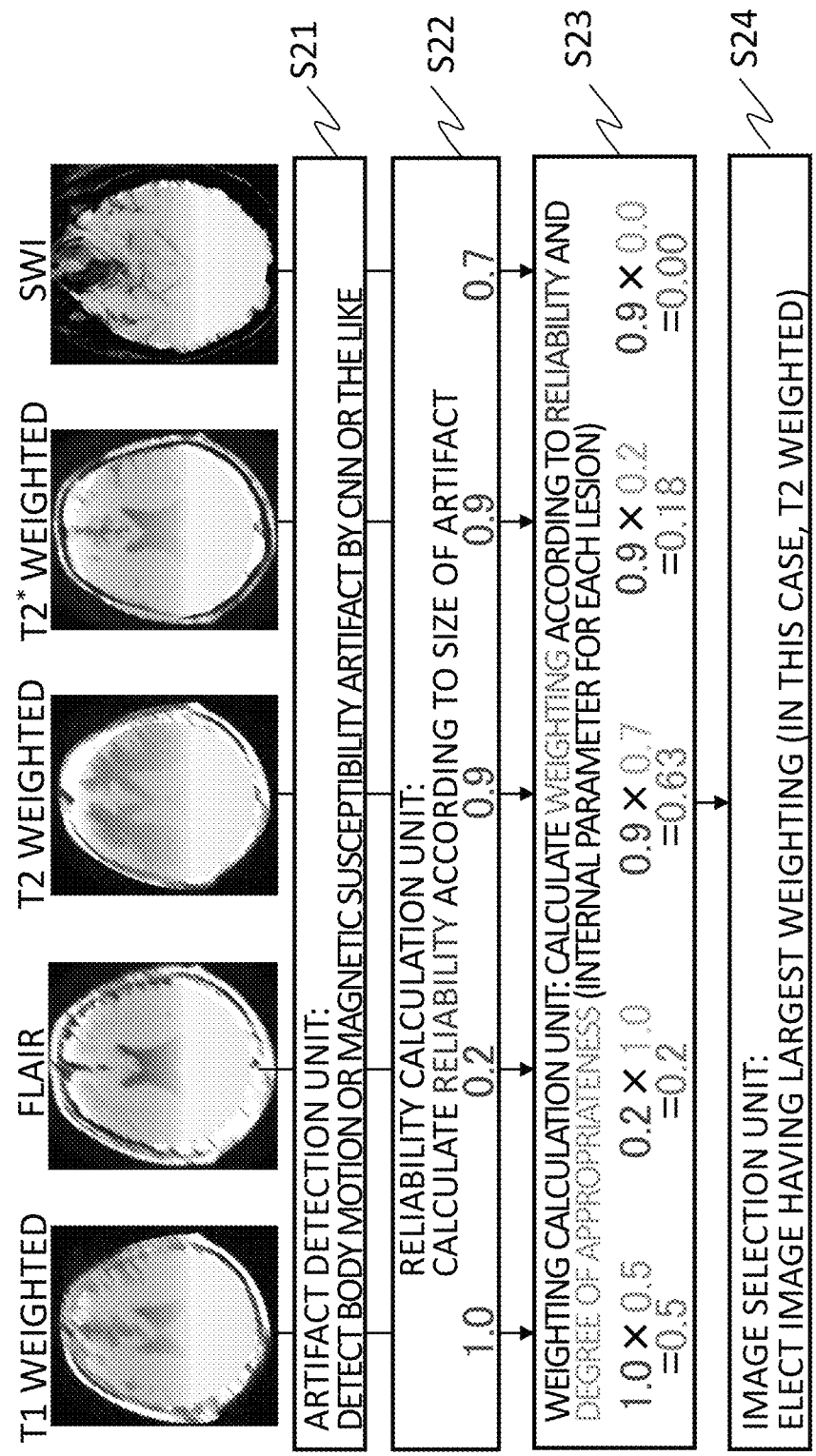
FIG. 5 is a diagram for describing a process for calculation of the degree of contribution and image selection in the first embodiment.
Figure 6:
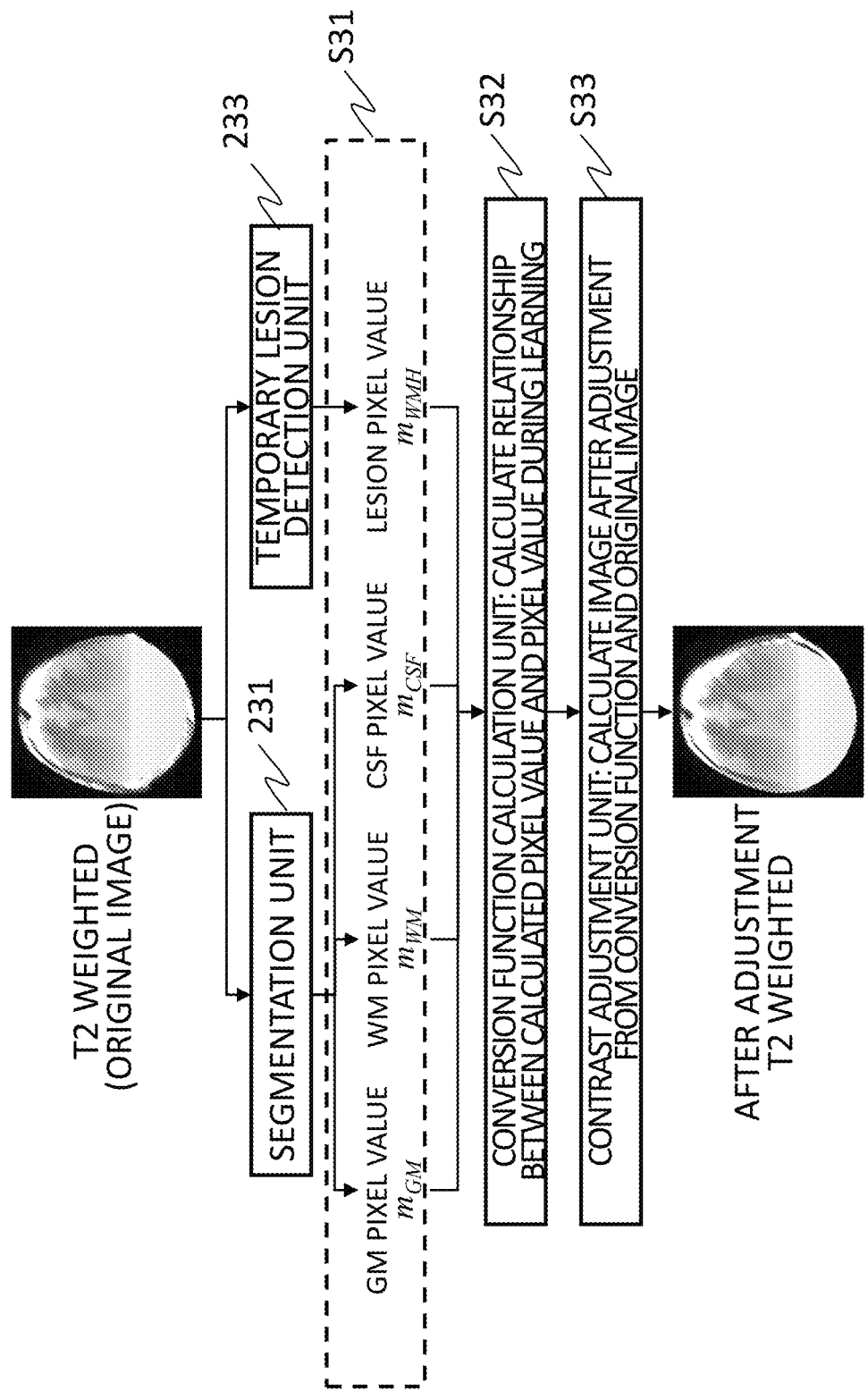
FIG. 6 is a diagram for describing a process of generating an image for detection in the first embodiment.

Hereinafter, the processing of each unit in the present embodiment will be described with reference to the flowchart illustrated in FIG. 3 and FIGS. 5 and 6. FIG. 5 is a diagram mainly illustrating the details of step S2 in FIG. 3, and FIG. 6 is a diagram mainly illustrating the details of step S3 in FIG. 3.

First, the image processing unit 20 receives a diagnostic target through the UI unit 30. Here, it is assumed that the diagnostic target is a cerebrovascular disease. The image processing unit 20 receives a plurality of images acquired in the examination of a cerebrovascular disease by the medical image acquisition apparatus (here, an MRI apparatus) 100 (FIG. 3: S1). The cerebrovascular disease is one diagnostic index for diagnosing vascular dementia, and the relationship between classification based on the cause of vascular dementia and cerebrovascular diseases, such as infarction, white matter lesions, and microbleed that are criteria for diagnosing the vascular dementia, is determined according to NINDS-AIREN diagnostic criteria. Then, types of MR images suitable for diagnosing the cerebrovascular diseases are also known. For example, FLAR is effective for diagnosing white matter lesions or infarction, and T2W is effective for infarction and perivascular expansion and T2*W or SWI is effective in diagnosing microbleeds. Therefore, the medical image acquisition apparatus 100 (MRI apparatus) acquires images, such as T1W, FLAIR, T2W, T2*W, and SWI, for the same subject in order to examine the cerebrovascular disease as illustrated in FIG. 5, and the image processing unit 20 receives the plurality of images (FIG. 3: S1).

The degree-of-contribution calculation unit 210 calculates the degree of contribution of each image to the diagnostic target (S1). Therefore, as illustrated in FIG. 5, first, an artifact is detected for each of the plurality of images input to the artifact detection unit 211 (S21). In order to detect an artifact, it is possible to use known methods, such as a method of detecting an artifact using a CNN (convolutional neural network) learned by using a large number of combinations of an image having no artifact and an image having an artifact and a method of detecting an artifact from a difference between an original image and an image from which an artifact is removed by a known artifact removal method. In this manner, the presence or absence and the size of an artifact having a large effect on the image quality, such as a body motion artifact or a magnetic susceptibility artifact are detected.

The reliability calculation unit 213 standardizes the size of the artifact detected by the artifact detection unit 211 to obtain an index of reliability (S22). In the example illustrated in FIG. 5, the reliability of 1.0, 0.2, 0.9, 0.9, and 0.7 is calculated as an example for five images. Here, the detection of an artifact may be performed for the entire image. However, the image may be divided into a plurality of regions to detect an artifact, and the reliability may be calculated for each region. Alternatively, the reliability may be calculated for each slice of the image. In this case, as the reliability of the image, addition (weighted addition) of the reliability of each of the portions can be used.

Then, the weighting calculation unit 215 calculates a weighting using the internal parameter and the reliability of each image calculated by the reliability calculation unit 213 (S23). The internal parameter is an index indicating the degree of appropriateness for the diagnostic target (lesion) for each image type, and is determined in advance and stored in the storage device 40, for example, in the form of a table shown in FIG. 7. In the example illustrated in FIG. 5, it is assumed that, for example, internal parameters of 0.5, 1.0, 0.7, 0.2, and 0.0 are set for five images.

The weighting can be calculated by a function using two values, such as a product or a sum of the "reliability" and the "internal parameter", and is determined so that the sum of the weightings of a plurality of images becomes 1. In the example illustrated in FIG. 5, the product of the reliability and the internal parameter is simply set as a weighting.

The image selection unit 220 selects one image or a predetermined number of images from the plurality of images according to the calculated weighting (S24). That is, an image having a largest weighting or top two images are selected. Here, it is assumed that one image, for example, a T2 weighted image is selected.

Figure 3:
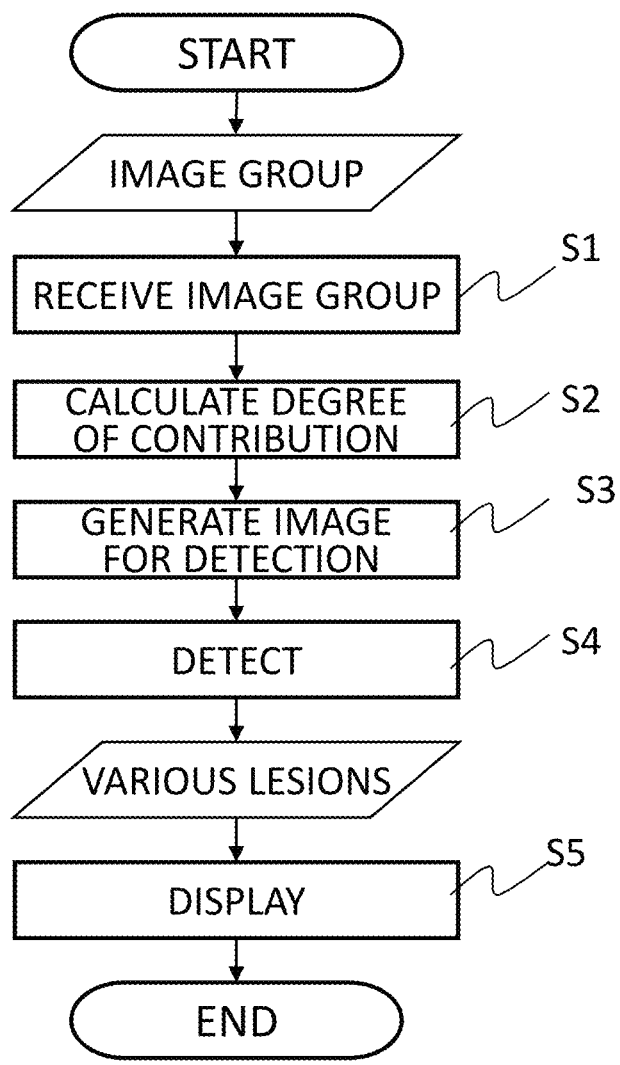
FIG. 3 is a flowchart illustrating an outline of processing of the image diagnosis support apparatus.

When one image is selected by the image selection unit 220, the image-for-detection generation unit 230 performs processing for matching the selected image (selection image) with the input image of the detection unit 250, that is, processing for converting the selected image into an image for detection input to the detection unit 250 (FIG. 3: S3). For this reason, as illustrated in FIG. 6, the segmentation unit 231 generates segmentation images by dividing the selection image into tissues, such as gray matter, white matter, and cerebrospinal fluid, and calculates a pixel value of each segmentation image (S31). The segmentation can be performed using a known method, such as an automatic segmentation algorithm using a threshold value or a convolutional neural network (CNN).

In addition, the temporary lesion detection unit 233 extracts a part having a high possibility of a lesion from the selection image, and calculates a pixel value of the part. Temporary detection of a lesion can be performed by lesion segmentation using a CNN or the like, similarly to the above-described segmentation. Unlike the final lesion detection performed by the detection unit 250, the temporary lesion detection performed herein is performed to improve the accuracy of processing for conversion into an image for detection, which will be described later, by calculating the pixel value for a part estimated to be a lesion. Therefore, it is preferable that the temporary lesion detection is performed, but it is also possible to omit the temporary lesion detection when the number of tissues divided by segmentation is large.

Figure 8:
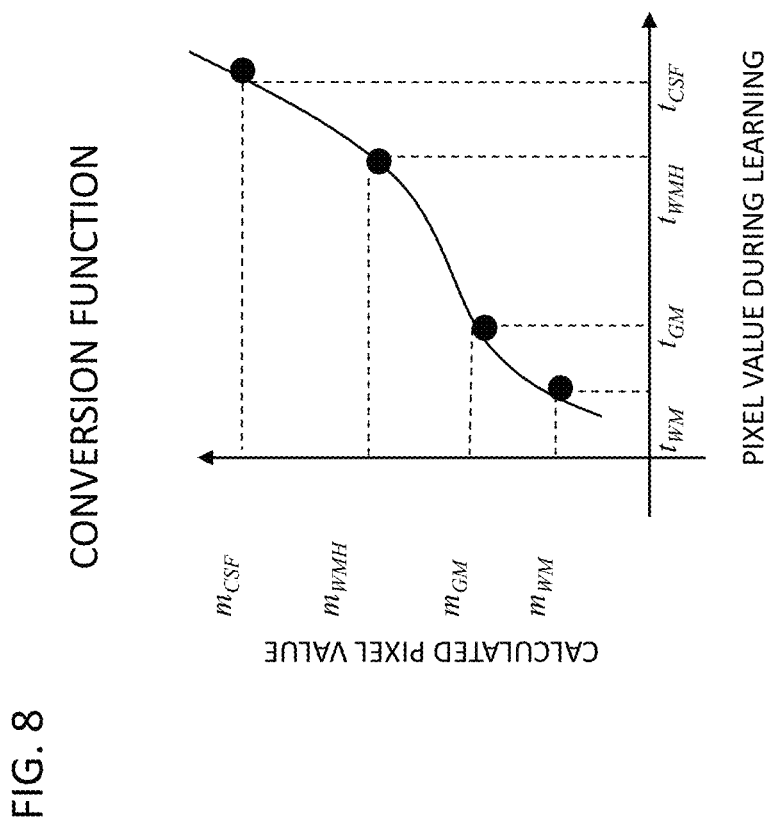
FIG. 8 is a diagram showing an example of a conversion function.

Then, the conversion function calculation unit 235 creates a conversion function using the pixel values (calculated pixel values) of each segmentation image and a lesion part calculated in step S31 and the pixel value (pixel value during learning) of the corresponding tissue of the image used by the detection unit 250 during learning (S32). As shown in FIG. 8, the conversion function can be obtained by plotting the calculated pixel value on a graph having the pixel value during learning on the horizontal axis and the calculated pixel value on the vertical axis and performing spline interpolation or fitting on the graph. Then, the contrast adjustment unit 260A generates an image for detection by applying the conversion function to each pixel of the selection image (S33). The examination image generated in this manner is an image adjusted such that the contrast is the same as that of the image used by the detection unit 250 at the time of learning.

Figure 9:
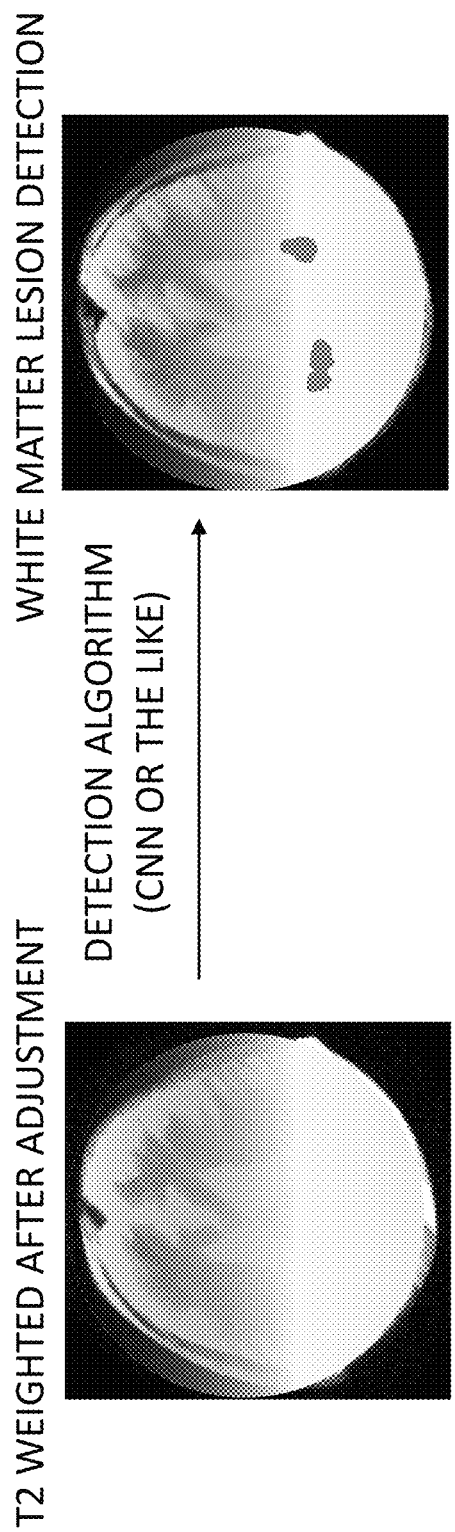
FIG. 9 is a diagram showing an example of a detection unit.

The examination image generated in step S33 is input to the detection unit 250 to obtain detection information. The detection unit 250 is configured by a detection algorithm of the CNN as shown in FIG. 9, and can take various forms according to what data is used as learning data. For example, detection information that is an output may be character information indicating the presence or absence or the degree of a lesion, or image information superimposed on an image, or both. In the example shown in FIG. 9, learning is performed so that a T2 weighted image is input and a white matter lesion detection result is output, and an image, an image showing, for example, a lesion position on the image in color (here, gray), and the like are output. The detection information output from the detection unit 250 is displayed on the display of the UI unit 30 (FIG. 3: S5).

According to the image diagnosis support apparatus of the present embodiment, even when there is an image unsuitable for lesion detection due to the influence of body motion or the like among a plurality of images, the most appropriate image can be automatically selected. Therefore, it is possible to improve the accuracy of lesion detection. In addition, the contrast of a plurality of input images varies depending on the vendor of the medical image acquisition apparatus, the magnetic field strength (in the case of the MRI apparatus), imaging conditions, and the like. However, according to the present embodiment, since the selected image is adjusted so as to have a contrast that matches that of the input image of the detection unit, it is possible to eliminate the influence of the difference from the contrast of the original image. Therefore, it is possible to improve the detection accuracy of the detection unit. As a result, useful support information can be provided.

In addition, in the present embodiment, when matching the selection image with the input image of the detection unit 250, the pixel values of the temporarily detected lesion part are also used to create a conversion function. Therefore, it is possible to perform contrast adjustment with high conversion accuracy.

Modification Example 1

In the above embodiment, a case has been described in which the presence or absence and the size of an artifact is used as an index of the reliability of a plurality of images. Instead of or in addition to the artifact, an SNR of an image may be used. The SNR of an image can be calculated by a known method, such as a method of calculating the SNR of an image from an average value and a standard deviation of pixel values of an arbitrarily set region of interest, and the reliability can be calculated by standardizing the SNR calculated for each image. Alternatively, the reliability calculated from the artifact and the reliability calculated from the SNR may be weighted and added to obtain the reliability.

Modification Example 2

In the above embodiment, a case has been described in which the contrast adjustment unit 260A adjusts the contrast of the selection image to the contrast of the learning image of the detection unit 250. However, when the selection image is an MR image, contrast adjustment between image types having different contrasts can also be performed, so that other contrast images are used as selection images. For example, when the image selected by the image selection unit 220 is a T1 weighted image but a T2 weighted image is suitable for the diagnostic target, the contrast of the T1 weighted image may be adjusted to the contrast of the T2 weighted image, which is a learning image, after performing adjustment to match the contrast of the T1 weighted image with that of the T2 weighted image that has not been adopted. Although the contrast of the T1 weighted image may be directly adjusted to the contrast of the learning image, it is possible to perform contrast adjustment while keeping the original information to the maximum by adjusting the contrast of the T1 weighted image to the contrast of the T2 weighted image measured as described above.

Modification Example 3

In the above embodiment, a case is illustrated in which MRI images having different contrasts are processing targets and one of the image types is selected. However, a plurality of images of the same image type but having different slice positions may be processing targets. Even in the case of images having different slice positions, as the internal parameter, the degree of appropriateness of the most appropriate cross-sectional position for the diagnostic target is set to the largest value, and the value of the internal parameter is set to decrease as the distance from the most appropriate cross-sectional position increases or as the angle with respect to the cross-sectional position increases. The calculation of the reliability using an artifact or the SNR is the same as in the first embodiment. In addition, as for the calculation of the reliability, instead of calculating the reliability for each image type, the reliability may be calculated for each region of a part of the image, for each pixel, or for each slice position when the image is three-dimensional data.

Second Embodiment

Figure 10:
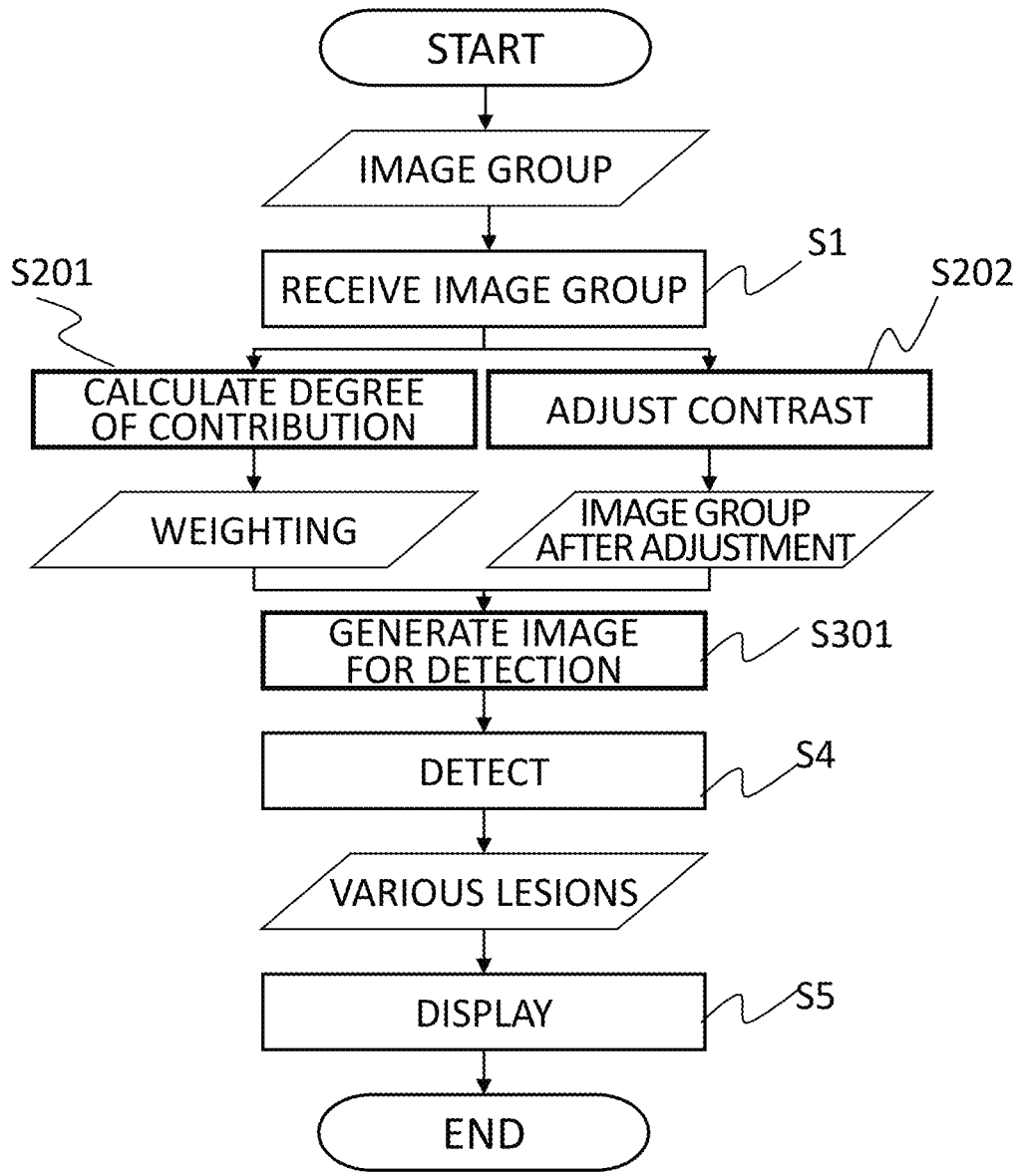
FIG. 10 is a diagram for describing the flow of processing according to a second embodiment.

In the first embodiment, a case has been described in which the image selection unit selects one image from a plurality of input images to generate an image for detection. In the present embodiment, however, an image for detection is generated using a plurality of input images. Also in the present embodiment, the configuration of the image processing unit 20 is almost the same as the configuration in the first embodiment illustrated in FIGS. 2 and 4, but the image selection unit 220 can be omitted. In addition, in the first embodiment, the contrast adjustment unit 260A is a functional unit of the image-for-detection generation unit 230. In the present embodiment, however, contrast adjustment may be performed by the contrast adjustment unit 260 before the generation of an image for detection. Hereinafter, the processing of the image processing unit 20 of the present embodiment will be described with reference to the flowchart of FIG. 10. In FIG. 10, the same processes as those in FIG. 3 are denoted by the same reference numerals, and repeated description thereof will be omitted.

After the detection of an artifact or the calculation of the SNR and the calculation of the reliability based on the artifact detection or the SNR calculation, the weighting calculation unit 215 calculates the weight (degree of contribution) of the plurality of input images using the reliability and the internal parameters (S201). The method of calculating the reliability and the method of calculating the weighting are the same as those in the first embodiment. The reliability may be calculated using the artifact or the SNR for the entire image, or the reliability may be calculated for each portion of the image, for example, for each slice, a plurality of regions, or each pixel. In the first embodiment, the image selection unit 220 selects an image having a largest weighting. In the present embodiment, however, the image-for-detection generation unit 230 performs weighted addition of a plurality of images without selecting an image. In order to add images, first, the contrast adjustment unit 260 performs contrast adjustment between a plurality of images (S202). For the contrast adjustment, as in the first embodiment, by the segmentation unit 231 and the conversion function calculation unit 235, segmentation and temporary lesion detection are performed on each of the plurality of images, and a conversion function (FIG. 8) is calculated using the pixels of each tissue and lesion and the pixels of the learning image. The contrast adjustment unit 260 applies the conversion function to the plurality of original images to obtain images whose contrast has been adjusted.

Then, an image for detection is generated by combining a plurality of images after the contrast adjustment using the weighting calculated in step S201 (S301). The combination using the weighting is weighted addition for each pixel. Here, when the reliability is calculated for each portion (for each tissue, each pixel, or the like) of the image, weighted addition is performed for each portion. Therefore, since a portion of the image having a very low reliability has a very small weighting, the portion of the image having a very low reliability hardly contributes to an image for detection. As a result, an image for detection reflecting the information of a portion having a high reliability is obtained. In addition, an image in which the internal parameter (appropriateness for the diagnostic target) is set to 0 depending on the diagnostic target has a weighting of 0, and the information is not reflected on the image for detection. As a result, only the image having a high degree of contribution is used for lesion detection and the like. In addition, when the weighting of an image having a largest weighting is set to "1" and the weighting of other images is set to "0", the processing of the weighted addition (image combination) of the present embodiment is the same as the image selection result in the first embodiment. In the meaning, the first embodiment can be regarded as a special example of the present embodiment.

Since a composite image has already been adjusted such that the contrast matches the contrast of the learning image of the detection unit 250 in step S202, the composite image becomes an input image of the detection unit 250 as it is as an image for detection. The detection unit 250 receives the image for detection and outputs a predetermined detection result (diagnosis support information).

According to the present embodiment, information of a plurality of images is weighted and added to generate an image for detection and detection of a lesion or the like is performed. Therefore, for a lesion and the like for which diagnosis using a plurality of images is considered appropriate, it is possible to detect a lesion with high accuracy without wasting the information of the plurality of image. In addition, since an image for generating an image for detection is weighted based on the reliability of the image, it is possible to prevent the reliability of the image for detection from lowering.

While the processing of the second embodiment has been described above, the modification examples of the first embodiment can also be applied to the present embodiment as they are.

Third Embodiment

The present embodiment is the same as the first and second embodiments up to the generation of an image for detection. However, the diagnostic information generation unit 240 has a function of performing analysis processing (FIG. 2: analysis unit 270) in addition to the lesion detection function of the detection unit 250 using a machine learning algorithm.

The analysis unit 270 performs processing, such as calculation of the area of a lesion part or calculation of the number of bleeding parts (microbleeds), using the image for detection. In addition, when the diagnostic target is the brain, a numerical value such as the calculated lesion area or the calculated number of bleeding parts is analyzed for each tissue using a brain atlas, and the analysis result is presented to the user through the UI unit.

The processing of the analysis unit 270 will be described with reference to FIGS. 11 and 12, taking the case of brain analysis as an example.

Figure 11:
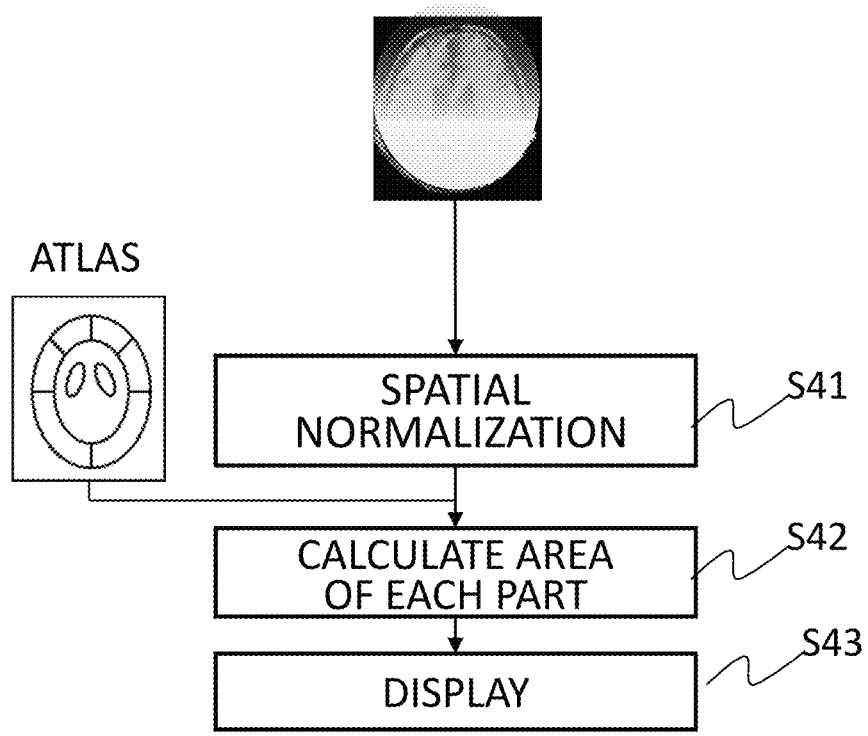
FIG. 11 is a diagram for describing an example of processing of an analysis unit according to a third embodiment.

In the case of calculating the area of a lesion, as illustrated in FIG. 11, spatial normalization of an image for detection is performed (S41). As for a brain image, a brain image with an average shape and size calculated from brain images of a large number of subjects acquired in advance is known as a standard brain. The spatial normalization is processing for converting an image to be analyzed into a standard brain image. As a conversion method, methods such as affine transformation and non-rigid registration are known. The analysis unit 270 includes a conversion module using such a method, and converts the image for detection into the brain coordinates of the standard brain. In the spatially normalized image, the tissue information (in the case of gray matter, information thereof) indicated by the pixel values includes the information of the original image. For example, according to the coordinate transformation, the coordinates of a certain tissue change and the area of the tissue is reduced or enlarged. However, the integrated value of the pixels forming the tissue remains as information, so that the area information is maintained.

A brain atlas that defines each region of the brain, for example, the parietal, frontal, temporal, and occipital regions, is applied to the conversion image obtained in this manner, and the area of the region specified in the brain atlas is calculated using the information of each tissue maintained at the time of conversion (S42). The calculated area is displayed on a display or the like in an arbitrary display form (S43).

Figure 12:
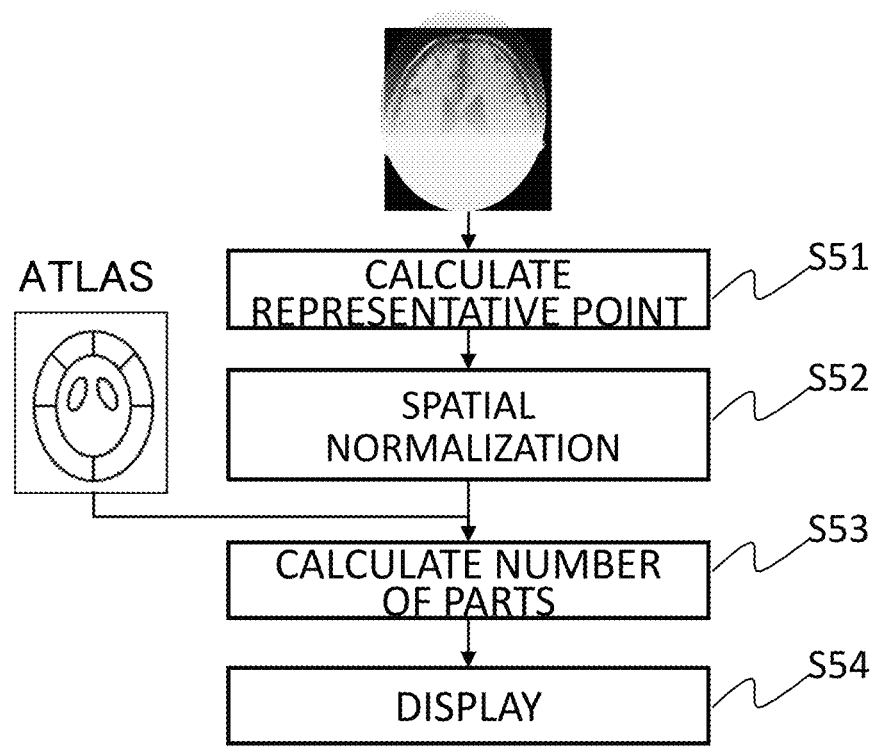
FIG. 12 is a diagram for describing another example of the processing of the analysis unit according to the third embodiment.

In the case of calculating the number, as illustrated in FIG. 12, the position of the bleeding is first specified in the image for detection, and its representative point is calculated (S51). Since the bleeding has a certain extent of spread, for example, the center of the bleeding is set as a representative point. The bleeding position can be specified by performing lesion segmentation using the pixel value of the lesion.

Then, spatial normalization of the image for detection is performed in the same manner as the spatial normalization in calculating the area, and conversion into the coordinates of the standard brain is performed (S52). At this time, information regarding the number of representative points is stored together with the position information. The position of the representative point changes with the conversion. When the bleeding part has a spread, some parts may overlap. However, since the information of the representative point (one point) does not overlap, the information can also be calculated as the position of one point even after the conversion. By applying the brain atlas to the image after the conversion, the number of representative points included in each brain region is counted (S53).

Figure 13A:
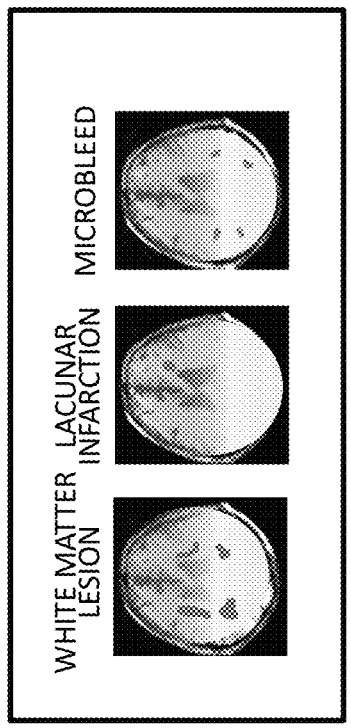
FIGS. 13A and 13B are diagrams showing display examples of the third embodiment.
Figure 13B:
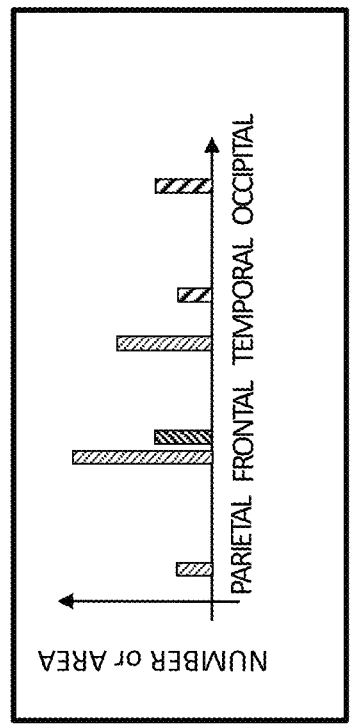

The analysis unit 270 displays the area or the number of bleeds calculated by the processing of steps S41 and S42 or S51 to S53 on the display of the UI unit 30 as numerical values or graphs (S54). FIGS. 13A and 13B show display examples. In the examples shown in FIGS. 13A and 13B, for example, the area of white matter and the number of microbleeds are shown as a bar graph for each brain region together with a brain image showing a brain lesion as a colored region (shown in gray in FIG. 13A). The user (doctor) can grasp the region of the brain where a white matter lesion or bleeding has occurred or the severity thereof by looking at such a display. Therefore, it becomes easy to determine the risk of stroke, vascular dementia, and the like based on the presence or absence or the degree of each lesion.

In addition, the calculation of the area of the tissue or the number of bleeds is merely an example, and analyses other than the exemplified analysis, such as the presence or absence or the degree of a brain tumor, can also be performed by the same means.

In addition, in the above embodiment, the description has been made focusing mainly on the brain image. However, the image diagnosis support apparatus of the invention can be similarly applied to lesions, such as a tumor in the abdomen or chest, as well as a brain disease.

In addition, in the above embodiment, the image diagnosis support apparatus independent of the medical image acquisition apparatus has been described. However, the function of the image diagnosis support apparatus of the invention can be realized by an image processing unit included in a medical image acquisition apparatus, such as an MRI apparatus or a CT apparatus.

Figure 14:
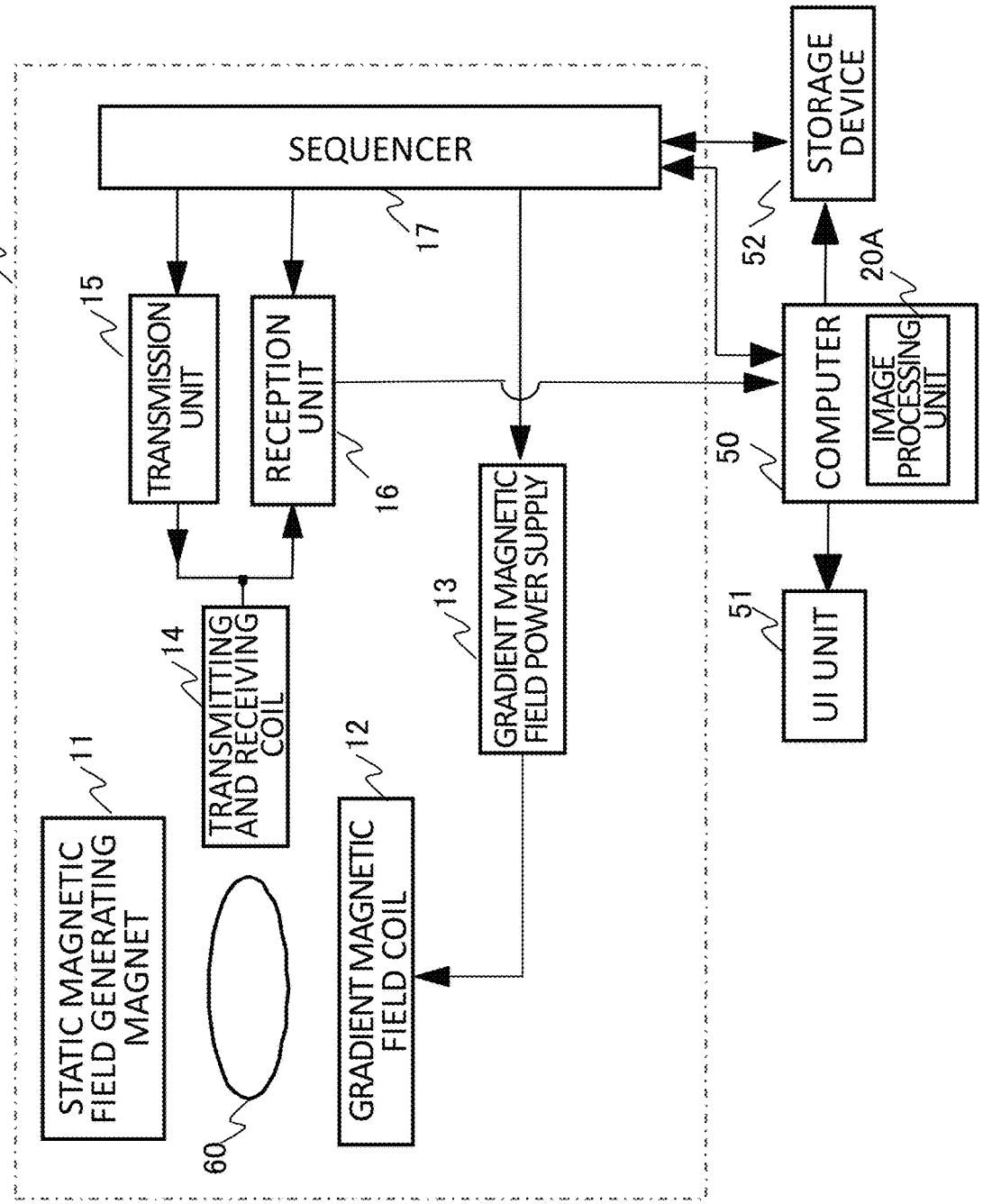
FIG. 14 is a diagram illustrating an overall outline of an MRI apparatus to which the invention is applied.

FIG. 14 illustrates an embodiment of an MRI apparatus as an example of the medical image acquisition apparatus 100 having a function of an image diagnosis support apparatus. An MRI apparatus 100A includes: an imaging unit 10 including a static magnetic field generating magnet 11 for generating a static magnetic field in a space where a subject 60 is placed, a gradient magnetic field coil 12, a gradient magnetic field power supply 13 (gradient magnetic field generation unit 12), a transmitting and receiving high-frequency coil 14, and a transmission unit (including a high frequency generator or a high frequency amplifier) 15 and a reception unit (including a quadrature detector or an A/D converter) 16 connected thereto; a sequencer 17 for controlling each of the units according to a predetermined pulse sequence; and an image processing unit 20A that processes a nuclear magnetic resonance signal received by the reception unit 16 and performs an operation, such as image reconstruction.

The function of a control system that controls the image processing unit 20A and the entire apparatus can be realized by a computer 50 including a CPU or a GPU and a memory, and it is possible to display the result of the image processing unit 20A or input commands or data required for processing of the image processing unit 20A or the control of the apparatus through a UI unit 51 configured to include a display or an input device attached to the computer. In addition, the processing result of the image processing unit 20A or data being processed can be stored in a storage device 52. The MRI apparatus 100A is the same as a general MRI apparatus except that the image processing unit 20A has an image diagnosis support function and control and display associated with the image diagnosis support function are added. That is, the functional block diagram of the image processing unit 20A is the same as that of the image processing unit 20 of the image diagnosis support apparatus of the above embodiment illustrated in FIGS. 1 and 2. For example, an image diagnosis support program for performing processing according to the flowchart illustrated in FIG. 3 is installed.

The detection result of the detection unit 250 of the diagnostic information generation unit 240 or the analysis result in a case in which the analysis unit 270 is further provided is displayed on the display of the UI unit 51. In addition, information required to operate the image diagnosis support function, for example, a command to specify a predetermined lesion is given to the image processing unit 20A through the input device of the UI unit 51.

In the MRI apparatus 100A, the imaging unit 10 operates according to the pulse sequence and the imaging conditions set by the user, so that an image having a desired contrast determined by the pulse sequence and the imaging conditions can be acquired. In the examination using the MRI apparatus 100A, the type of image to be acquired is determined in advance as a protocol together with the imaging order. When the MRI examination is performed according to such an examination protocol, the execution of the image diagnosis support function may be added in advance to a part of the protocol, so that necessary types of images are automatically acquired and the image diagnosis support function using these images is executed. For example, the imaging unit 10 executes a plurality of imaging sequences using a predetermined pulse sequence and imaging parameters in an order defined by a protocol, and acquires a plurality of types of images, such as T1W and T2W. The image processing unit 20A receives the plurality of types of images, and generates and presents diagnostic information.

While an example has been described in which the image diagnosis support apparatus of the invention is applied to the MRI apparatus, a medical image acquisition apparatus other than the MRI apparatus can also have an image diagnosis support function as an image processing unit.

What is claimed is:

1. An image diagnosis support apparatus, comprising:
a memory coupled a processor, the memory storing instructions that when executed configure the processor to:
train a machine learning algorithm using a plurality of training images to detect a tissue,
evaluate an image reliability for each of a plurality of medical images,
calculate a degree of contribution of each of the plurality of medical images to a diagnostic target based on a sum or a product of the image reliability and a degree of appropriateness of each medical image for a diagnostic target tissue, the degree of appropriateness being a predetermined value stored in a table, the degree of appropriateness selected from the table based on a type of each medical image and the diagnostic target tissue,
adjust a contrast of one or more of the plurality of medical images to be a same contrast of the training images using one or more conversion functions,
generate an image for detection by subjecting the adjusted images to weighted addition based on the calculated degree of contribution of each of the plurality of medical images, and
input the generated image for detection to the trained machine learning algorithm to detect a presence or an absence of the diagnostic target tissue in the generated image for detection as a detection result, which indicates the presence or absence of the diagnostic target tissue.

2. The image diagnosis support apparatus according to claim 1,
wherein the processor is configured to divide an image into a plurality of regions or portions and calculate a reliability for each region or each portion.

3. The image diagnosis support apparatus according to claim 1,
wherein the processor is configured to calculate the reliability based on an artifact included in the medical image or a signal noise ratio of the medical image.

4. The image diagnosis support apparatus according to claim 1,
wherein the processor is configured to:
select an image among the plurality of medical images having a greatest weight, and
calculate a pixel value for a part of the selected image estimated to include the diagnostic target tissue.

5. A non-transitory computer-readable medium storing an image diagnosis support program causing a computer to execute steps comprising:
training a machine learning algorithm using a plurality of training images to detect a tissue;
calculating an image reliability for each of a plurality of medical images;
calculating a degree of contribution of each of the plurality of medical images to a diagnostic target based on a sum or a product of the image reliability and a degree of appropriateness of each medical image for a diagnostic target tissue, the degree of appropriateness being a predetermined value stored in a table, the degree of appropriateness selected from the table based on a type of each medical image and the diagnostic target tissue;
adjust a contrast of one or more of the plurality of medical images to be a same contrast of the training images using one or more conversion functions,
generate an image for detection by subjecting the adjusted images to weighted addition based on the calculated degree of contribution of each of the plurality of medical images,
input the generated image for detection to the trained machine learning algorithm to detect a presence or an absence of the diagnostic target tissue in the generated image for detection, detection result, which indicates the presence or absence of the diagnostic target tissue.

6. The non-transitory computer-readable medium according to claim 5, the steps further comprising:
selecting an image among the plurality of medical images having a greatest weight; and
calculating a pixel value for a part of the selected image estimated to include the diagnostic target tissue.

7. A medical image acquisition apparatus, comprising:
a memory coupled a processor, the memory storing instructions that when executed configure the processor to:
train a machine learning algorithm using a plurality of training images to detect a tissue,
evaluate an image quality and calculates an image reliability for each of a plurality of medical images,
calculate a degree of contribution of each of the plurality of medical images to a diagnostic target based on a sum or a product of the image reliability and a degree of appropriateness of each medical image for a diagnostic target tissue, the degree of appropriateness being a predetermined value stored in a table, the degree of appropriateness selected from the table based on a type of each medical image and the diagnostic target tissue,
adjust a contrast of one or more of the plurality of medical images to be a same contrast of training images using one or more conversion functions,
generate an image for detection by subjecting the adjusted images to weighted addition based on the calculated degree of contribution of each of the plurality of medical images, and
input the generated image for detection to the trained machine learning algorithm to detect a presence or an absence of the diagnostic target tissue in the generated image for detection, as a detection result, which indicates the presence or absence of the diagnostic target tissue.

8. The medical image acquisition apparatus according to claim 7,
wherein the imaging unit is a magnetic resonance imaging unit that collects a nuclear magnetic resonance signal of a subject and acquires a medical image using the nuclear magnetic resonance signal, and
wherein the plurality of medical images include at least one of a T1 weighted image, a T2 weighted image, a proton density weighted image, a FLAIR image, a magnetic susceptibility weighted image, and a diffusion weighted image as types of images.

9. The medical image acquisition apparatus according to claim 7,
wherein the plurality of medical images are brain images, and
the diagnostic target generation unit generates information regarding a cerebrovascular disease as the diagnostic information.

10. The medical image acquisition apparatus according to claim 7,
wherein the processor is configured to:
select an image among the plurality of medical images having a greatest weight, and
calculate a pixel value for a part of the selected image estimated to include the diagnostic target tissue.

* * * * *